(12) United States Patent
Elangovan et al.

(10) Patent No.: US 10,976,227 B2
(45) Date of Patent: Apr. 13, 2021

(54) MAGNETIC ENRICHMENT OF MAGNETICALLY MARKED ANALYTES

(71) Applicant: INDIAN INSTITUTE OF TECHNOLOGY DELHI, New Delhi (IN)

(72) Inventors: Ravikrishnan Elangovan, New Delhi (IN); Vivekanandan Perumal, New Delhi (IN); Shalini Gupta, New Delhi (IN); Saurabh Singh, New Delhi (IN); Mohita Upadhyay, New Delhi (IN)

(73) Assignee: INDIAN INSTITUTE OF TECHNOLOGY DELHI, New Delhi (IN)

( * ) Notice: Subject to any disclaimer, the term of this patent is extended or adjusted under 35 U.S.C. 154(b) by 470 days.

(21) Appl. No.: 15/552,248

(22) PCT Filed: Nov. 16, 2015

(86) PCT No.: PCT/IN2015/050168
§ 371 (c)(1),
(2) Date: Aug. 18, 2017

(87) PCT Pub. No.: WO2016/132375
PCT Pub. Date: Aug. 25, 2016

(65) Prior Publication Data
US 2018/0038778 A1    Feb. 8, 2018

(30) Foreign Application Priority Data
Feb. 19, 2015    (IN) .............................. 485/DEL/2015

(51) Int. Cl.
*G01N 21/00* (2006.01)
*G01N 1/40* (2006.01)
(Continued)

(52) U.S. Cl.
CPC ............ *G01N 1/4077* (2013.01); *B01L 3/502* (2013.01); *B03C 1/01* (2013.01); *B03C 1/0332* (2013.01);
(Continued)

(58) Field of Classification Search
CPC ....................... G01N 35/0098; G01N 35/1074
(Continued)

(56) References Cited

U.S. PATENT DOCUMENTS 5,779,907 A * 7/1998 Yu .................... B01L 3/5085
210/695
2006/0223178 A1 10/2006 Barber et al.
(Continued)

*Primary Examiner* — Natalia Levkovich
(74) *Attorney, Agent, or Firm* — Procopio, Cory, Hargreaves & Savitch LLP

(57) ABSTRACT

The present subject matter describes system (100) for magnetic enrichment of magnetically marked analytes. The system has capture chip (102) comprising a sample chamber (104) for holding sample having magnetically marked analytes, and a recovery chamber (106) connected to the sample chamber by a channel (202). The volume of recovery chamber is smaller than volume of sample chamber (104). The system has magnetic arrangement (108) comprising a set of magnets (110) in which each two adjacent magnets have opposite polarities facing sample chamber. Set of magnets has dimensions that at least conform to coverage area of sample chamber. The magnetic arrangement also has at least one recovery magnet (112) having dimensions conforming to coverage area of recovery chamber and on alignment, the at least one recovery magnet (112) is at a distance farthest away from the recovery chamber. The system has a linear positioner (114) for moving the magnetic arrangement.

3 Claims, 6 Drawing Sheets

(51) Int. Cl.
  *B03C 1/28* (2006.01)
  *B03C 1/01* (2006.01)
  *C12M 1/00* (2006.01)
  *B03C 1/033* (2006.01)
  *B01L 3/00* (2006.01)
  *C12N 15/10* (2006.01)

(52) U.S. Cl.
  CPC ............. *B03C 1/288* (2013.01); *C12M 47/04* (2013.01); *C12N 15/1013* (2013.01); *B01L 2200/0647* (2013.01); *B01L 2400/043* (2013.01); *B01L 2400/06* (2013.01); *B03C 2201/22* (2013.01); *B03C 2201/26* (2013.01); *G01N 2001/4038* (2013.01)

(58) Field of Classification Search
  USPC ................................................ 422/554, 527
  See application file for complete search history.

(56) References Cited

U.S. PATENT DOCUMENTS

| | | |
|---|---|---|
| 2007/0059718 A1 | 3/2007 | Toner |
| 2014/0087414 A1 | 3/2014 | Hayden |

\* cited by examiner

US 10,976,227 B2

MAGNETIC ENRICHMENT OF MAGNETICALLY MARKED ANALYTES

CROSS-REFERENCE TO RELATED APPLICATIONS

This application is a U.S. National Stage entry of International Patent Application No. PCT/IN2015/050168, filed on Nov. 16, 2015, which claims priority to Indian Patent Application No. 485/DEL/2015, filed Feb. 19, 2015, the contents of which are incorporated herein by reference.

TECHNICAL FIELD

The present subject matter relates, in general, to enrichment of analytes and, in particular, to magnetic enrichment of magnetically marked analytes.

BACKGROUND

Enrichment refers to the process of increasing the concentration of a particular type of analyte present in a sample. The enrichment of analytes, also referred to as target analytes, may be done by reducing the volume of the solvent of the sample, while maintaining the initial number of target analytes in the sample. The enrichment of analytes may also be done by removing other background materials, such as cells, proteins, and toxins, which are present in the sample alongside the target analyte. Enrichment of target analyte to smaller volume increases the concentration of target analyte in the sample, thereby improving sensitivity of detection of target analytes by existing detection methods, such as enzyme-linked immunosorbent assay (ELISA), polymerase chain reaction (PCR), lateral flow assay, and agglutinations assay. Further, the enrichment of target analyte to smaller volume removes background materials that might interfere with detection assay.

BRIEF DESCRIPTION OF DRAWINGS

The features, aspects, and advantages of the subject matter will be better understood with regard to the following description, and accompanying figures. The use of the same reference number in different figures indicates similar or identical features and components.

DETAILED DESCRIPTION

Figure 1A:
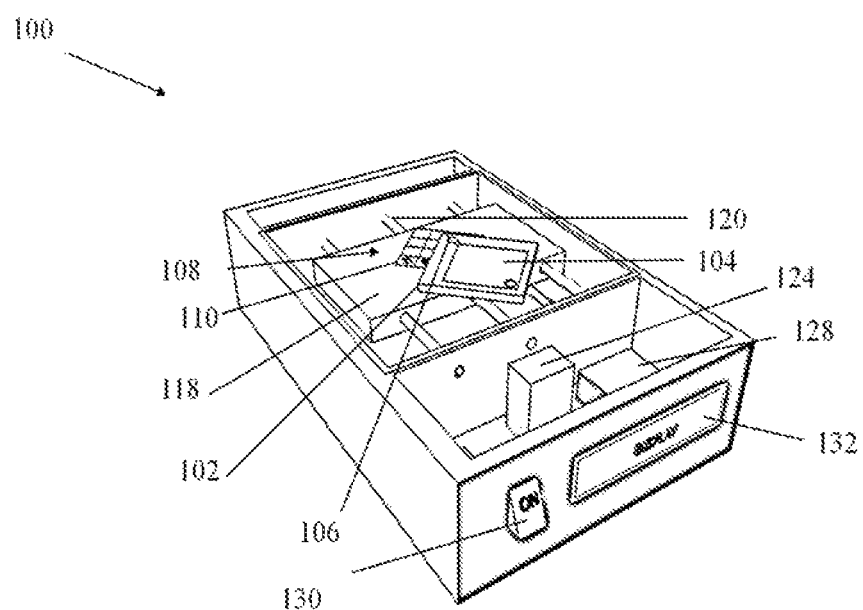
FIGS. 1(a) and 1(b) illustrate a system for magnetic enrichment of magnetically marked analytes, in accordance with an implementation of present subject matter.

The subject matter disclosed herein relates to systems to magnetically enrich the magnetically marked analytes. The analytes may include cells, viruses, proteins, toxins, nucleotides, etc.

A variety of analytes may be present in low concentrations in a sample, for instance, a liquid bio-sample. There may be a need to separate or detect a particular type of analytes, hereinafter referred to as the target analytes, from the sample. The enrichment of the target analytes that are present in the sample may be achieved by reducing the volume of the solvent of the sample in a manner such that the number of target analytes within the sample is not reduced. Further, the target analytes in a sample may also be enriched by reducing the number of other analytes, toxins, background organic materials, and the like, that are initially present in the sample alongside the target analytes. Hence, enrichment may be seen as increasing the concentration of the target analytes in a sample.

The target analytes present in a sample can be enriched by marking the target analytes with magnetic particles and subjecting the magnetically marked analytes to a magnetic field. The application of magnetic field on the magnetically marked analytes results in their coagulation or capture within a region where magnetic field is strong. This technique of enriching of the magnetically marked analytes may be referred to as magnetic enrichment.

Conventionally, the magnetic enrichment of magnetically marked analytes is done by pumping the sample through a magnetic region. The magnetic region is a region that is under the influence of a magnetic field. Hence, when the magnetically marked analytes are pumped through the magnetic region, the magnetically marked analytes settle down due to the influence of the magnetic field.

Conventional systems for magnetic enrichment of magnetically marked analytes use a pumping system to facilitate pumping of the sample through the magnetic field. The pumping system may comprise one or more pumps, valves, and connecting tubes for the pumps, and other components for passing the sample through the magnetic region. The inclusion of pumps, valves, and connecting tubes to the system increases the complexity of the system and adds to the cost of the system.

Further, pumping of a high viscosity liquid sample may clog the pumping system, thereby resulting in erratic flow of the sample. The pumping systems may also be prone to cracks or leaks, often near the joints and the bends in the pumping system. The cracks and leaks may result in the leakage of the sample or other liquids passing through the pumping system. The leakage of the sample or the other liquids may cause inefficient capturing and enrichment of the target analytes. Also, due to the leakage, a person using the system may be accidently exposed to the leaked sample, which may be potentially harmful. Leakages and pump tubings may also increase the chance of cross contamination between the samples.

Further, in the conventional systems, the processing time of the sample for magnetic enrichment is substantially high, for example, enrichment of 100 nm magnetic particles in 1 ml can take about 20 minutes at flow rate of 50 µl/min. Larger the sample volume, higher is the processing time taken for magnetic enrichment. This is due to the dependence of the processing time on the maximum rate at which a sample can be passed through the systems. Since, the maximum rate of the conventional magnetic enrichment systems is low, the processing time of the sample for the magnetic enrichment is high.

The present subject matter describes systems for magnetic enrichment of magnetically marked analytes from a sample. The sample may be understood as a liquid bio-sample, and the magnetically marked analytes may be understood as target analytes that are marked with magnetic particles. The system includes a capture chip having a sample chamber and a recovery chamber. The sample chamber holds the sample under the influence of a magnetic field, while the recovery chamber is a chamber where the target analytes are eventually captured. The volume of the recovery chamber is smaller as compared to the volume of the sample chamber.

The system also includes a magnetic arrangement that provides a magnetic field to capture the magnetically marked analytes in the sample chamber and to drag the magnetically marked analytes into the recover chamber. The magnetic arrangement has a set of magnets, where the set of magnets has dimensions that at least conform to a coverage area of the sample chamber. The coverage area of the sample chamber may be understood as the area of spread of the sample that is poured in the sample chamber. The magnetic arrangement also has at least one recovery magnet, each of which at least has dimensions that conform to the coverage area of the recovery chamber. The role of the at least one recovery magnet is to facilitate dragging of the magnetically marked analytes into the recovery chamber, in accordance with the present subject matter.

The system further includes a linear positioner to move the magnetic arrangement with respect to the capture chip. The magnetic arrangement is mounted on the linear positioner such that the magnetic arrangement is moved along an axis or a line passing through the recovery chamber and the at least one recovery magnet.

For the purpose of magnetic enrichment of the magnetically marked analytes, the magnetic arrangement is aligned with the capture chip such that the set of magnets is under the sample chamber, and the at least one recovery magnet is at a distance farthest away from the recovery chamber. The sample is injected into the sample chamber. The sample may be held with respect of magnetic arrangement in a fixed position for a predefined time depending on the volume of the sample. For example, for a sample volume of about 7.5 ml, the sample may be held in the sample chamber for about 5 minutes. The sample is held in the sample chamber to allow the magnetically marked analytes to settle at the base of the sample chamber under the influence of a magnetic field from the set of magnets of the magnetic arrangement. After the predefined time, the magnetic arrangement is moved along the axis passing through the recovery chamber and the at least one recovery magnet with the help of the linear positioner. This results in dragging of the magnetically marked analytes towards the recovery chamber. The magnetic arrangement is moved until the at least one recovery magnet, that lies at the farther end from the set of magnets, is under the recovery chamber, so that the magnetically marked analytes are eventually dragged into the recovery chamber. The recovery chamber has a substantially smaller volume as compared to the sample chamber. Thus, the magnetically marked analytes are captured within the recovery chamber and are hence magnetically enriched within a substantially small volume.

The systems of the present subject matter can enrich the magnetically marked target analytes without using a pumping system. The absence of the pumping system makes the systems simple in configuration and reduces the cost of the systems. The absence of the pumping system substantially eliminates the clogging and leakages of the sample or other liquids from the system. This further ensures the safety of any individual operating the system, who might otherwise be at a risk of being exposed to the sample leaking out of the system. In one implementation, the capture chip may be a use and throw capture chip. The use and throw capture chip minimizes the cross contamination between the samples.

The systems of the present subject matter enrich the magnetically marked analytes without the use of any pumping system, and hence, they do not suffer from issues related to the low flow rates. The systems of the present subject matter can enrich the magnetically marked analytes in a substantially smaller time in comparison to the conventional systems. The systems of the present subject matter can enrich the magnetically marked analytes from a sample of volume upto 30 ml in about 15 minutes.

These and other advantages of the present subject matter would be described in greater detail in conjunction with the following figures. It should be noted that the description and figures merely illustrate the principles of the present subject matter.

Figure 1B:
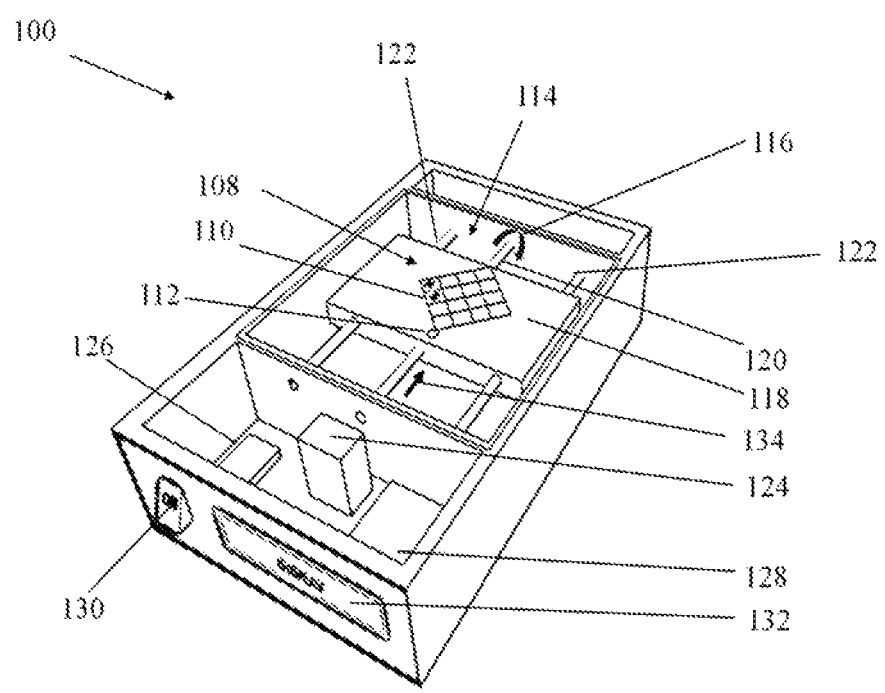

FIGS. 1(a) and 1(b) illustrate a system 100 for magnetic enrichment of magnetically marked analytes present in a sample, in accordance with an implementation of present subject matter. The sample may be understood as a liquid sample that comprises analytes that are marked with magnetic particles. The analytes may be one of proteins, bacteria, mammalian cells, organic cells, toxins, antibodies, virus, and the like. The system 100 comprises a capture chip 102 as shown in FIG. 1(a). The capture chip 102 has two chambers, namely, a sample chamber 104 and a recovery chamber 106. The sample chamber 104 is used for holding the sample having magnetically marked analytes. The sample chamber 104 is connected to the recovery chamber 106 by a channel. The recovery chamber 106 of the capture chip 102 is the region where the magnetically marked analytes are captured after the system operation. Thus, the recovery chamber 106 has a smaller volume as compared to the sample chamber 104.

The system 100 further comprises a magnetic arrangement 108 for providing a magnetic field to the sample in the sample chamber 104 and the recovery chamber 106. The capture chip 102 is placed above the magnetic arrangement 108 such that the distance between the capture chip 102 and the magnetic arrangement 108 is at most 2 mm. The magnetic arrangement 108 comprises of a set of magnets 110. The set of magnets 110 has dimensions that at least conform to a coverage area of the sample chamber 104. The magnets in the set of magnets 110 are placed such that a pole of each magnet faces the capture chip 102. Also, the magnets belonging to the set of magnets 110 are so arranged that each pair of adjacent magnets has opposite polarities facing the capture chip 102.

The magnetic arrangement 108 further comprises a recovery magnet 112, adjoined to the set of magnets 110. The recovery magnet 112 has dimensions that conform to the coverage area of the recovery chamber 106.

The system 100 further comprises a linear positioner 114 for moving the magnetic arrangement 108 with respect to the capture chip 102. The linear positioner 114 moves the magnetic arrangement 108 with respect to the capture chip 102 along an axis passing through the recovery chamber 106 and the recovery magnet 112. The linear positioner 114 comprises a base plate 118 on which the magnetic arrangement 108 is mounted. The base plate 118 is coupled to a screw rail 120 which may be rotated about its longitudinal axis to move the base plate 118 and hence, the magnetic arrangement 108. The base plate 118 is further coupled to linear support rails 122 which provide additional support and directivity to the base plate 118. The system 100 further comprises a stepper motor 124. The stepper motor 124 is coupled with the screw rail 120 in order to rotate the screw rail 120 about its longitudinal axis. The rotation of the screw rail 120 in one direction facilitates the movement of the base plate 118 in a particular direction. For example, the rotation of the screw rail 120 in clockwise direction, referenced as 116, may move the base plate 118 in a direction referenced as 134. The speed of rotation of the stepper motor 124 controls the speed of movement of the base plate 118 and hence, of the magnetic arrangement 108. The system 100 includes a microcontroller 126 that can be programmed to control the speed of rotation of the stepper motor 124, and hence, the speed of movement of the magnetic arrangement 108. The linear positioner 114 shown herein is an example implementation of a linear positioner. Any other type of linear positioner may also be used that can maintain the velocity and range of the movement.

The system 100 also comprises an AC-DC convertor 128 coupled to the stepper motor 124, the microcontroller 126, and other electronic components of the system 100 for their operation. The system 100 further comprises a switch 130 which can be operated to turn on or off the system 100. The system 100 includes a LCD display 132 that displays current status of the system operation. For example, the LCD 132 may display "Instrument Ready" when the system 100 is ready for operation, and display "Capture ON" when the process of capturing of the magnetically marked analytes, by the system 100, is ongoing. Further, the LCD 132 may also display "Time Left: XX minutes" to signify the time remaining until the system 100 completes the operation.

Figure 2:
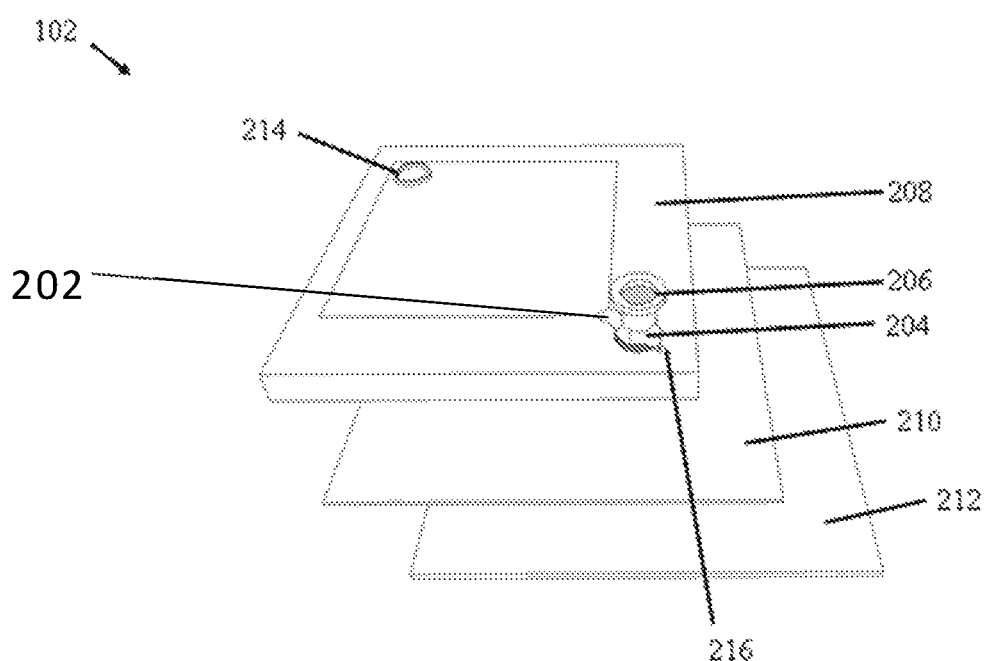
FIG. 2 illustrates a layered structure of a capture chip of the system, in accordance with an implementation of the present subject matter

FIG. 2 illustrates a layered structure of the capture chip 102 of the system 100, in accordance with an implementation of the present subject matter. The capture chip 102 comprises a three layered structure. The three layers of the capture chip 102 include a first layer 208, a second layer 210, and a third layer 212. The orientation of the three layers of the capture chip 102 is such that the second layer 210 is sandwiched between the first layer 208 and the third layer 212, with the first layer 208 lying on top. The first layer 208 has a block-like structure that may be made of one of Polydimethylsiloxane (PDMS), Polymethyl methacrylate (PMMA), flexible plastic, and the like. The first layer 208 has two hollow regions formed by creating grooves on the surface of the first layer 208, to which the second layer 210 is to be attached. One of the two hollow regions has more coverage area, and hence, more volume, than the other hollow region. The two hollow regions when covered from below, form the sample chamber 104 and the recovery chamber 106 such that, the sample chamber 104 a larger coverage area and volume than the recovery chamber 106.

The sample chamber 104 may be of dimensions such that it can hold the sample of volume ranging from about 1 ml to about 30 ml. In the implementation shown in FIG. 2, the sample chamber 104 has a square shaped coverage area. The recovery chamber 106 lies near one of the corners of the sample chamber 104 such that the recovery chamber 106 is located on an axis along a diagonal of the sample chamber 104. In one implementation, the length of each side of the sample chamber 104 having a square shaped coverage area is about 5 cm while the depth of the sample chamber 104 may be about 3 mm. Such a sample chamber 104 can hold about 7.5 ml of sample. In an implementation, the dimensions of the recovery chamber 106 are such that it can hold a sample volume ranging from about 5 µl to about 50 µl.

As shown, the hollow regions of the sample chamber 104 and the recovery chamber 106 are connected to each other by another hollow region forming a channel 202. The channel 202 is fabricated creating a groove on the PDMS block of the first layer 208. Further, the two chambers 104 and 106 and the channel 202, all have a base, i.e., the surface that lies near to the magnetic arrangement 108 when magnetic arrangement 108 aligns with the capture chip 102. The surface of the two chambers 104 and 106, and the channel 202 that lies opposite to the respective bases has three openings. The first opening forms an inlet 214 through which the sample is poured inside the sample chamber 104. The second opening, hereinafter referred to as an outlet 216, coincides with the recovery chamber 106 and may be used to collect the captured analytes from the recovery chamber 106. The third opening is in the channel 202 and forms a valve gap 204 which is described in the following description. It may be noted that the channel, along with the valve gap 204, is aligned on the axis along diagonal of the sample chamber 104 on which the recovery chamber 106 is located.

The sample chamber 104 and the recovery chamber 106 may be isolated from each other by a valve cap 206. The channel 202 may be blocked by placing the valve cap 206 in the valve gap 204. The valve cap 206 may be made of one of Teflon™, Acrylonitrile butadiene styrene (ABS), Nylon, and the like. By blocking the channel 202, the sample chamber 104 is isolated from the recovery chamber 106. The isolation of the two chambers 104 and 106 may be done after the operation of the system 100 is complete, i.e., the magnetically marked analytes are captured in the recovery chamber 106.

The second layer 210 of the capture chip 102 is a polymer layer having a thickness about 100 µm. The second layer 210 is attached with the first layer 208 such that the second layer 210 forms the base of the sample chamber 104, the recovery chamber 106, and the channel 202. In one implementation, the second layer 210 may be fabricated by coating the third layer 212 with one of paraffin, bovine serum albumin (BSA), and Polyethylene glycol (PEG). Due to the coating of the third layer 212, the base of the sample chamber 104, the recovery chamber 106, and the channel 202 is coated with one of the above mentioned materials and thus prevents the non specific binding of the magnetically marked analytes to the surface of the base.

The third layer 212 of the capture chip 102 may be made up of hard plastic and is used for providing mechanical integrity to the capture chip 102. As mentioned in the earlier description, the second layer 210 is a thin polymer layer of thickness 100 µm. Due to thinness of the second layer 210, the mechanical integrity of the capture chip may be reduced, thus rendering the structure of the capture chip 102 weak. Thus, the third layer 212 is provided to improve the mechanical integrity of the capture chip 102 and hence, facilitate a proper operation of the system 100.

Figure 3:
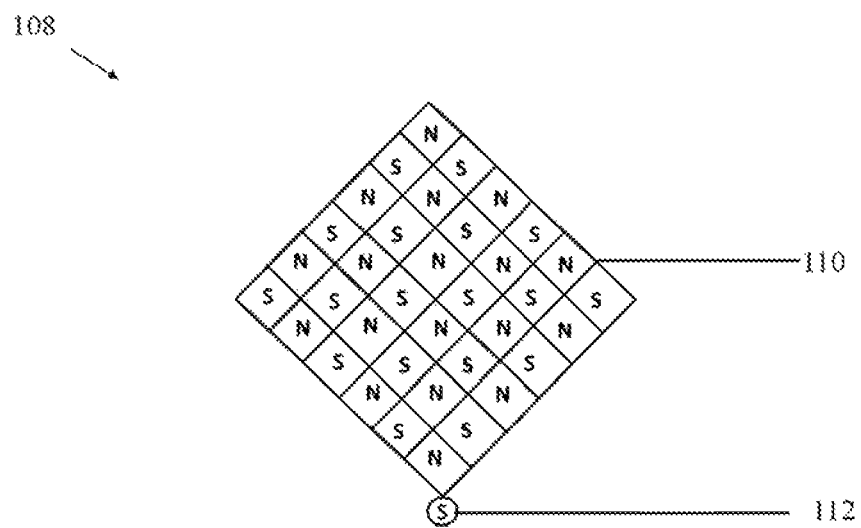
FIG. 3 illustrates a magnetic arrangement of the system, in accordance with an implementation of the present subject matter.

FIG. 3 illustrates the magnetic arrangement 108 of the system 100, in accordance with an implementation of the present subject matter. The magnetic arrangement 108 comprises of a set of magnets 110 which is formed by an N*N square grid magnets and whose dimensions at least conform to the coverage area of the sample chamber 104. The number of magnets in each row of the set of magnet may range from 6 to 10, depending on the dimensions of the sample chamber 104. As depicted in FIG. 3, the set of magnets 110 is a 6*6 square grid of magnets, i.e., the number of magnets in each row of the set of magnets 110 is 6. In an implementation, the cross-section of the magnets of the set of magnets 110 is square. In one implementation, the width of the magnets may range from about 5 mm to about 15 mm and the height of the magnets may range from about 3 mm to about 20 mm. The magnets of the set of magnets 110 are arranged in a manner that each two adjacent small magnets have opposite polarities facing the capture chip 102, as shown. Also, the dimensions of the set of magnets 110 conform to the shape of the coverage area of the sample chamber 104. The similar shape and dimensions of the set of magnets 110 and the magnetic arrangement 108 ensures that the sample chamber lies under the influence of a magnetic field.

The magnetic arrangement 108 further comprises one recovery magnet 112 having dimensions that at least conform to the coverage area of the recovery chamber 106. The recovery magnet 112 enables the dragging of the magnetically marked cells into the recovery chamber 106. As shown in FIG. 3, the recovery magnet 112 has a circular shape with a diameter of about 5 mm. The recovery magnet 112 is placed at one corner of the square shaped set of magnets 110 in a manner that the recovery magnet 112 lies on an axis passing through a diagonal of the set of magnets 110. In another implementation, the magnetic arrangement may comprise more than one recovery magnet, as described later in FIG. 4.

In another implementation of the system 100, the magnetic arrangement 108 may comprise an isolated magnet (not shown) adjoined to the set of magnets 110, where the isolated magnet has dimensions that at least conform to the coverage area of the recovery chamber 106. For the square shaped magnetic arrangement 108, the isolated magnet is placed near the corner of the set of magnets 110 which is diagonally opposite to the corner at which the recovery magnet 112 is present. The placement of the isolated magnet is such that initially, when the capture chip 102 is placed above the magnetic arrangement 108, the isolated magnet aligns with the recovery chamber 106. The isolated magnet with the recovery chamber 106 ensures that the recovery chamber 106 lies under the influence of a magnetic field while the sample is initially allowed to settle in the sample chamber 104.

Figure 4:
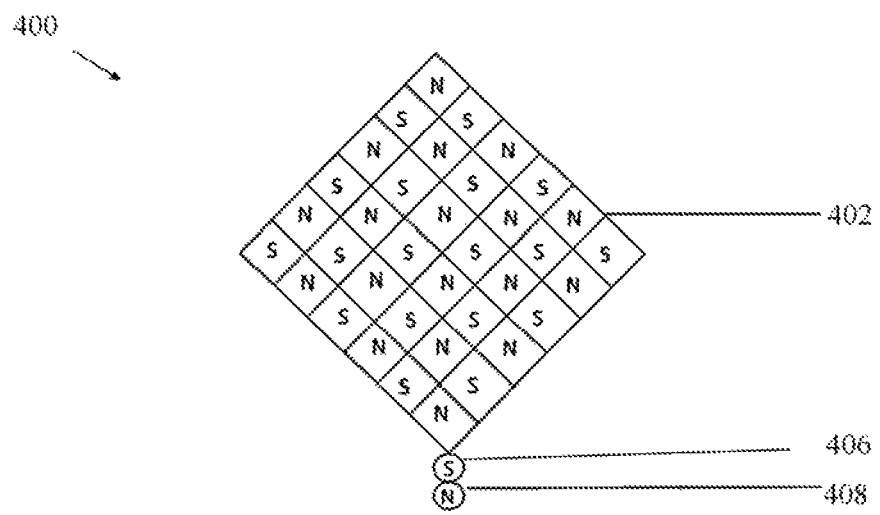
FIG. 4 illustrates a magnetic arrangement of the system, in accordance with another implementation of the present subject matter.

FIG. 4 illustrates the magnetic arrangement 400 of the system 100, in accordance with another implementation of the present subject matter. The magnetic arrangement 400 as illustrated in FIG. 4 has a set of magnets 402 similar to the magnetic arrangement 108 as depicted in FIG. 3. The magnetic arrangement 400 has two recovery magnets, unlike the magnetic arrangement 108 with one recovery magnet 112. Each of the recovery magnets, namely a first recovery magnet 406 and a second recovery magnet 408, has dimensions that conform to the coverage area of the recovery chamber 106. The first recovery magnet 406 and the second recovery magnet 408 are together adjoined at one of the corners of the set of magnets 402, as shown. It may be noted that in this implementation, the south pole of the first recovery magnet 406 faces the capture chip 108 on alignment of the capture chip 108 with magnetic arrangement 400. Similarly, the north pole of the second recovery magnet 408 faces the capture chip on alignment of the capture chip 108 with magnetic arrangement 400. As explained in the previous description, the magnetic arrangement 400 is moved with respect to the capture chip 102 along an axis passing through the recovery chamber 106 and two recovery magnets 406 and 408. Also, the movement of magnetic arrangement 108 is continued until the second recovery magnet 408 aligns with the recovery chamber 106.

Even though this description covers implementations with one recovery magnet and two recovery magnets adjoined to the magnetic arrangement, other implementations, of the present subject matter, with more than two recovery magnets are also possible.

In an implementation, the coverage area of sample chamber may be circular in shape. In this implementation, the sample chamber has a circular base. Further, the sample chamber having a circular shaped coverage area is connected to a recovery chamber by a channel. Similar to the other implementation, the recovery chamber has a smaller volume as compared to the sample chamber. The sample chamber, as a part of a capture chip, may be placed on a magnetic arrangement having a set of magnets similar to the set of magnets 110, and having dimensions that at least conforms to the coverage area of the sample chamber. Further, the magnetic arrangement has at least one recovery magnet adjoined to the set of magnetic arrangement. The at least one recovery magnet is adjoined to the magnetic arrangement such that the recovery chamber lies diametrically opposite to the at least one recovery magnet when the capture chip is initially placed above the magnetic arrangement. Also, the set of magnets is arranged such that each two adjacent magnets of the set of magnets have opposite polarities facing the capture chip.

The following description describes the preparation of the sample having magnetically marked analytes. In one implementation, the sample may be a liquid sample having analytes that are marked with magnetic particles. The magnetic particles may be one of paramagnetic, super-paramagnetic, and ferromagnetic. Further, the size of the magnetic particle may lie in a range from about 50 nm to about 5000 nm. For example, the magnetic particle may be a paramagnetic particle of size 100 nm. Initially, the magnetic particles may be conjugated with a binding agent, for example, antibodies, aptamers, peptides, or probes which can bind specifically with the analyte to be captured. After conjugation of the magnetic particles with the binding agent, the conjugated magnetic particles are incubated with the sample having unconjugated analytes for a period of time. This period of time may vary from about 10 minutes to about 120 minutes. As a result of the incubation, the analytes get conjugated with magnetic particles through the binding agent and the sample is prepared.

The description hereinafter describes the operation of the system 100 for magnetic enrichment of analytes. Initially, the capture chip 102 is placed above the magnetic arrangement 108 such that the distance between the magnetic arrangement 108 and the capture chip 102 is at most 2 mm. Further, the capture chip 102 is placed over the magnetic arrangement 108 such that the set of magnets 110 aligns with the sample chamber 104. As a result, the sample chamber 104 is under the influence of a magnetic field produced by the set of magnets 110 of the magnetic arrangement 108. Also, the capture chip 102 is placed over the magnetic arrangement 108 in a manner that the recovery chamber 106 and the recovery magnet 112 lie at a distance farthest away from each other, i.e., at the diagonally opposite ends. Further, in the implementation where the magnetic arrangement has the isolated magnet adjoined to the set of magnets, the capture chip 102 is placed above the magnetic arrangement in a manner that the recovery chamber 106 aligns with the isolated magnet. This causes the recovery chamber 106 to be under the influence of a magnetic field.

The sample having the magnetically marked analytes is poured in the sample chamber 104. Since the sample chamber 104 is under the influence of the magnetic field from below, the magnetically marked analytes of the sample experience a magnetic force and settle at the base of the sample chamber 104. The sample is held in the sample chamber 104 for a period of time depending on the volume of the sample, i.e., about 5 minutes for 7.5 ml of sample. Since the base of the sample chamber 104 is made of parafilm® M or is coated with one of polyethylene glycol, bovine serum albumin, and casein, the non-specific binding of the magnetically marked analytes on the surface of base is prevented.

After this, the stepper motor 124, which may be controlled by a microcontroller 126, is operated to rotate the screw rail 120 which results in the movement of the base plate 118, and hence the magnetic arrangement 108 with respect to the capture chip 104. The movement of the magnetic arrangement 108 is along an axis passing through the recovery chamber 106 and the recovery magnet 112. In one implementation, the speed of movement of the magnetic arrangement 108 is about 1 cm per minute. As the magnetic arrangement 108 moves along the axis, the magnetic field produced by the magnetic arrangement 108 also moves. This results in a moving magnetic field across the sample chamber 104. Further, it causes the magnetically marked analytes, which had settled down at the base of the sample chamber 104, to be dragged along with the moving magnetic field. The dragging of the magnetically marked analytes along with the magnetic arrangement 108 continues until the recovery magnet 112 aligns with the recovery chamber 106, i.e., the recovery chamber 106 lies above the recovery magnet 112.

One may appreciate that when the recovery chamber 106 lies above the recovery magnet 112, the recovery chamber 106 experiences the magnetic field produced by the magnetic arrangement 108. Thus, the magnetically marked analytes are collected within the small volume of the recovery chamber 106. At this point, the valve cap 206 may be inserted in the valve gap 208, which blocks the channel 202 and isolates the sample chamber 104 from the recovery chamber 106. Hence, the magnetically marked analytes are captured within the recovery chamber 106.

In an implementation where the sample chamber 104 has a circular coverage area, the operation remains similar to the operation as described above. One may recall from the previous description that for such a case, upon alignment of capture chip with magnetic arrangement, the recovery chamber lies diametrically opposite to the recovery magnet. Further, the axis of movement of the magnetic arrangement along the line joining the recovery magnet and the recovery chamber.

It is to be noticed that the magnetically marked analytes are captured within a small volume of sample that is equivalent to the volume of the recovery chamber 106. This implies that the sample captured within the recovery chamber 106 has a higher concentration of magnetically marked analytes as compared to the sample poured in the sample chamber 104 at the start of the operation. Also, the volume of the solvent in the sample is reduced while maintaining the number of magnetically marked analytes that were initially present in the sample. Hence, the magnetically marked analytes are enriched by the system 100. The enriched magnetically marked analytes can be taken out from the recovery chamber and analyzed for a variety of purposes.

Figure 5A:
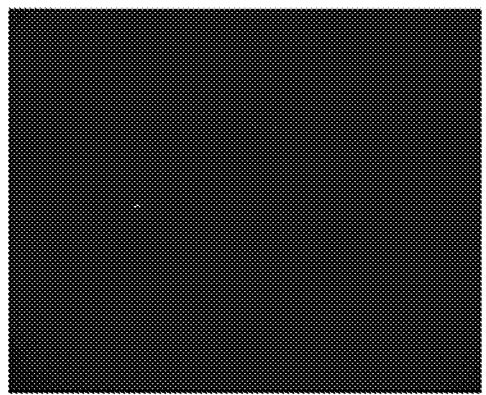
FIGS. 5(a) and 5(b) illustrate fluorescent images depicting the enriched cells imaged by optical detection technique, in accordance with an implementation of the present subject matter.
Figure 5B:
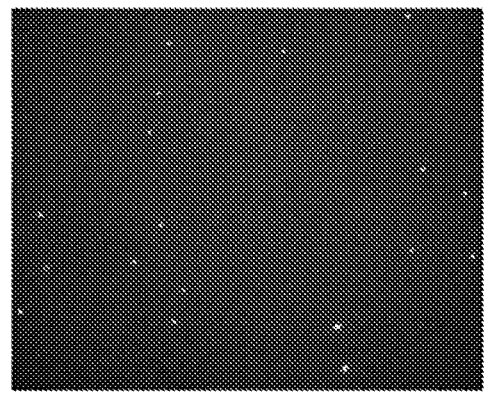

FIGS. 5(*a*) and 5(*b*) illustrate fluorescent images depicting the enriched cells imaged by optical detection technique, in accordance with an implementation of the present subject matter. The concentration of the cells in the sample is $10^6$ CFU/ml. In order to optically detect a particular type of analytes, in this case cells, from a sample, one may conjugate the analytes with fluorescent particles in addition to the conjugation with the magnetic particles. The fluorescent particles may be conjugated in the same manner as described earlier for conjugating the analytes with magnetic particles. Initially, the fluorescent particles may be conjugated to a binding agent, such as antibodies, aptamers, peptides, and probes. After conjugation of the fluorescent particles with the binding agent, the conjugated fluorescent particles, along with the conjugated magnetic particles, are incubated with the sample having the analytes for a period of time ranging from about 10 minutes to about 120 minutes. As a result of the incubation, the analytes get conjugated with the fluorescent particles and magnetic particles through the binding agent and the sample gets prepared.

The prepared sample may be viewed under a fluorescent microscope to detect the fluorescent particles which are conjugated with the particular type of analytes. FIG. 5(*a*) depicts an optical image of a sample whose cells are not enriched. FIG. 5(*b*) depicts an optical image of a sample whose cells are enriched by the system 100.

In the FIGS. 5(*a*) and 5(*b*), the illuminated spots depict fluorescent particles conjugated with cells that are to be enriched. The count of illuminated spots can be approximated to estimate the number of fluorescent particles, and thus estimate the number of conjugated cells of the sample enriched by system 100. As observable in the FIG. 5(*a*), one fluorescent particle, conjugated with a cell, is detected. However, in the FIG. 5(*b*), one observes about 20 fluorescent particles, each conjugated with a cell.

Although the present subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter.

We claim:

1. A system (100) for magnetic enrichment of magnetically marked analytes, wherein the system (100) comprises:
   a capture chip (102) comprising:
      a sample chamber (104) for holding a sample having the magnetically marked analytes; and
      a recovery chamber (106) connected to the sample chamber (104) by a channel (202), wherein volume of the recovery chamber (106) is smaller than volume of the sample chamber (104) wherein the recovery chamber (106) and the channel (202) are at a corner of the sample chamber (104) and are aligned along a diagonal of the sample chamber (104);
   a magnetic arrangement (108) comprising:
      a set of magnets (110) for providing an external magnetic field to the magnetically marked analytes in the sample chamber (104), wherein each two adjacent magnets of the set of magnets (110) have opposite polarities facing the sample chamber (104), and wherein the set of magnets (110) has dimensions that at least conforms to an area of the sample chamber (104) in which the sample is held; and
   at least one recovery magnet (112) at a corner of the set of magnets (110), wherein the at least one recovery magnet (112) has dimensions that at least conforms to an area of the recovery chamber (106) in which the magnetically marked analytes are dragged, and wherein the magnetic arrangement (108) is aligned with the capture chip (102) such that the at least one recovery magnet (112) is at a distance farthest away from the recovery chamber (106);
   a linear positioner (114) coupled to the magnetic arrangement (108); and
   a stepper motor (124) coupled to the linear positioner (114) to move the linear positioner (114) for moving the magnetic arrangement (108) with respect to the capture chip (102) along an axis passing through the recovery chamber (106) and the at least one recovery magnet (112), wherein the magnetic arrangement (108) is positioned with respect to the capture chip (102) such that the at least one recovery magnet (112) is located at a corner of the sample chamber (104) diagonally opposite to the corner thereof at which the recovery chamber (106) is located, and wherein the magnetic arrangement (108) is moved by the linear positioner (114) along the diagonal of the sample chamber (104).

2. The system (100) as claimed in claim 1, wherein the coverage area of the sample chamber (104) has a square shape.

3. The system (100) as claimed in claim 2, wherein the set of magnets (110) of the magnetic arrangement (108) are arranged in an N×N grid that conforms to the shape of the coverage area of the sample chamber (104).

* * * * *